United States Patent [19]

Manders

[11] Patent Number: 4,955,395
[45] Date of Patent: Sep. 11, 1990

[54] TISSUE EXPANDER AND METHOD OF TREATING MALE TEMPLE BALDNESS

[76] Inventor: Ernest K. Manders, 1 Timberline Pl., Hummelstown, Pa. 17036

[21] Appl. No.: 488,165

[22] Filed: Mar. 8, 1990

[51] Int. Cl.⁵ .......................... A61B 19/00; A61F 2/02
[52] U.S. Cl. .................................. 128/898; 128/899; 623/8; 623/11
[58] Field of Search ................................ 128/897–899; 623/8, 11; 606/192

[56] References Cited

U.S. PATENT DOCUMENTS

| | | | |
|---|---|---|---|
| 4,217,889 | 8/1980 | Radovan et al. | 623/8 X |
| 4,574,780 | 3/1986 | Manders | 128/898 |
| 4,685,447 | 8/1987 | Iversen et al. | 128/899 |
| 4,798,205 | 1/1989 | Bonomo et al. | 128/897 X |

*Primary Examiner*—Ronald Frinks
*Attorney, Agent, or Firm*—Thomas Hooker

[57] ABSTRACT

A tissue expander for expanding hair to cover temple bald recesses includes a base having a central arm and a pair of end arms separated by a pair of concave recesses and an expandable cover joined to the edge of the base.

15 Claims, 1 Drawing Sheet

TISSUE EXPANDER AND METHOD OF TREATING MALE TEMPLE BALDNESS

FIELD OF THE INVENTION

The invention relates to inflatable soft tissue expanders of the type adapted to be implanted beneath the hair bearing scalp and expanded to increase the area of the hair bearing scalp. After deflation and surgical removal of the expander, the hair bearing scalp is moved forward to cover a former bald area of the scalp.

DESCRIPTION OF THE PRIOR ART

Radovan U.S. Pat. No. 4,217,889 discloses a conventional soft tissue expander having a base and an overlying cover joined to the edge of the base. Fluid is injected into the cavity between the base and cover and expands the elastic cover and soft tissue overlying the cover.

Manders U.S. Pat. No. 4,574,780 discloses a specialized tissue expander which differentially expands overlying soft tissue. Pairs of this type of expander are used to differentially expand the hair bearing temporal scalp to either side of male pattern bald central scalp. Following surgical removal of the two expanders the expanded scalp is advanced to cover the former bald area.

C-shaped expanders, sometimes referred to as croissant expanders, have a pair of spaced arms separated by a single recess. These devices are used to expand skin surrounding a defect area so that following removal of the defect the expanded skin may be advanced and applied to cover the defect area.

SUMMARY OF THE INVENTION

The present invention is a specialized soft tissue expander having three spaced arms extending from one side of the base with concave recesses between the arms and a single interior cavity. The expander is implanted in a pocket the arms surrounding skin defects and expanded in a single operation to enlarge skin surrounding both defects. Following removal of the expander the skin is advanced to cover both defects in a single operation.

The expander may be used to treat temple bald recesses by expansion of the surrounding hair bearing scalp. In this treatment, the expander is implanted beneath the hair of a patient with temple bald recesses with the central arm underlying the central forelock, the end arms underlying the hair bearing temple area and the recesses of the expander generally conforming to the receding anterior hairline at the temple bald recesses. Inflation of the expander cover above the skull expands the overlying hair bearing scalp and permits advancement of the expanded scalp to cover both temple bald recesses. If desired, the forelock may also be moved forward a short distance to advance the central hairline.

The three armed expander surrounds both temple bald recesses and expands normal hair growing scalp to permit restoration of the normal male pattern hairline. Slight hair line concavities may be provided at the temples where expanded hair bearing scalp is advanced over the former temple bald recesses. The procedure is performed with a minimum of scar tissue located just forward of the anterior hairline. The scar line is not readily visible but may be concealed by hair, if desired.

The implanted expander is positioned under hair bearing scalp within a conforming pocket, with each arm fitted within a corresponding arm in the pocket. This arrangement assures that the expander is maintained in proper location in the pocket during expansion and greatly reduces the undesired possibility of shifting of the expander within the pocket. Shifting can cause non-uniform expansion of the overlying scalp rendering advancement impractical. Additionally, shifting may result in a portion of the expander erupting through the overlying soft scalp tissue. The ends of the arms are rounded to prevent eruption through overlying soft tissue during expansion.

Other objects and features of the invention will become apparent as the description proceeds, especially when taken in conjunction with the accompanying drawings illustrating the invention, of which there is one sheet and one embodiment.

IN THE DRAWINGS

DESCRIPTION OF THE PREFERRED EMBODIMENT

Figure 3:
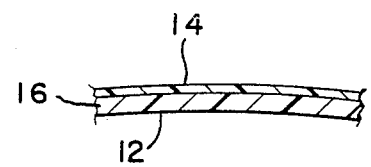
FIG. 3 is a sectional view taken along line 3—3 of FIG. 2.
Figure 2:
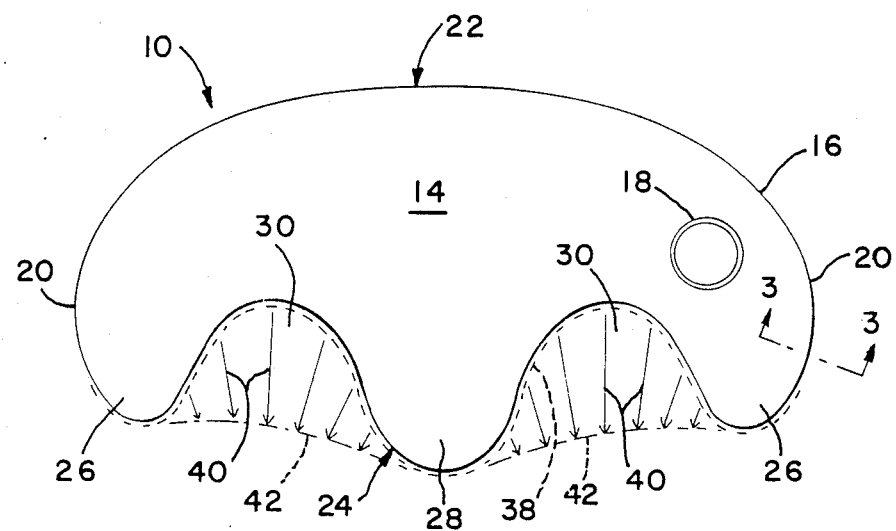
FIG. 2 is an enlarged view of the expander shown in FIG. 1.

Tissue expander 10 shown in FIGS. 2 and 3 is preferably formed from a biocompatible silicone elastomer and includes flexible non-extensible base 12 and expandable cover 14 on top of the base and integrally joined to the base at the peripheral edge 16 of the expander. When the expander is collapsed the cover and base overlie upon each other as indicated in FIG. 3. The expander is provided with suitable filling port 18 which is preferably mounted in cover 14. The cover 14 has a uniform thickness so that when fluid is injected into an implanted expander 10 through port 18 the cover is forced upwardly above the base and expands toward a hemispheric configuration as measured in transverse cross section. If desired, the base 12 may be provided with fiber reinforcement. The expander may include an integral closed body defining the interior of the expander as disclosed in U.S. Pat. No. 4,574,780. In expander 10 the cover and base are the same shape when the expander is deflated. Alternatively, the cover may have a larger area than the base and may be folded up when the expander is deflated.

As shown in FIG. 2 the base of expander 10 has a pair of longitudinally spaced apart ends 20 joined by peripheral sides 22 and 24. Side 22 is a smooth convex arc joining ends 20. Side 24 is generally sinuous and includes outwardly facing end arms 26, outwardly facing central arm 28 and a pair of inwardly facing convex recesses 30 located between arms 26 and 28. The arms and recesses are smoothly curved with the arms facing laterally of the expander, parallel to each other. This construction gives expander 10 a double-croissant or W-shape in top view. The ends of the arms 26 and 28 are smoothly rounded to prevent eruption during expansion.

Figure 1:
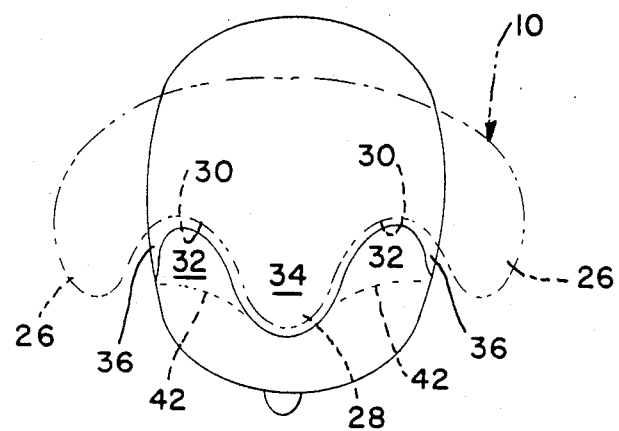
FIG. 1 is a top view illustrating a tissue expander according to the invention spread in a horizontal configuration and located above the head of a patient with a receding anterior hairline.

Tissue expander 10 is implanted under the scalp of a patient with a receding anterior hairline and temple bald recesses 32 of the type shown in FIG. 1. When placed down on the head, expander side 24 generally conforms to the anterior hairline of the patient at the top of the forehead with the central arm 28 conforming to the hairy forelock 34, the inner sides of the end arms 26 conforming to the upper edges of the hairy temple areas 36 and the edges of recesses 30 conforming to the edges of the full bald recesses on the scalp.

The tissue expander 10 is implanted by forming an incision 38 (as indicated in FIG. 2) along the patient scalp line, lifting the hair bearing scalp from the skull to form a pocket having the shape of the expander and then inserting the expander into the pocket so that the fingers and recesses are positioned to conform closely to the hairline. The hairline incision is then sutured closed to confine the deflated expander within the pocket.

After an appropriate interval saline solution is injected into the single interior cavity of the expander through port 18 so that cover 14 and overlying hairy soft tissue are expanded above the base 12 which is supported on the skull. Repeated injection of saline solution into the expander lifts the cover and expands the overlying tissue thereby increasing the area of the hair bearing scalp around the two temple bald recess defects 32 located between adjacent arms 26 and 28.

Expansion is continued until the measured arc length of the expanded scalp indicates sufficient expansion has occurred to cover the temple recesses. Normally, sufficient expansion occurs when the scalp has been raised approximately four to five centimeters above the skull. This relatively small degree of expansion can be easily concealed by wearing a hat, such as a baseball cap, to lessen patient embarrassment during the period of expansion.

After completion of expansion, fluid is drained from the expander and another incision is formed along side 24 to sever the expanded scalp at the hairline and permit removal of the deflated expander. At this time, the bald scalp at temple areas 32 is surgically removed and the expanded hair bearing scalp surrounding each of the defect sites 32 is advanced as indicated generally by arrows 40 to form advanced temple hairlines 42. The anterior-posterior width of expander 10 assures that with expansion of the hair bearing scalp surrounding and behind the defect areas 32 sufficient additional hair bearing scalp is formed to be brought forward and completely cover the defects. The expanded tissue is easily bunched along the new hairline 42 and sutured to the remaining skin at the top of the forehead. In time, the expanded tissue grows flat on the skull with a minimum scar at the hairline. If desired, the expanded forelock may be advanced anteriorly a slight distance.

While I have understood and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A tissue expander including a base, an expandable cover overlying the base and joined to the peripheral edge of the base to define an interior chamber, and port means for inflating the chamber, the base including three spaced arms separated by two recesses.

2. A tissue expander as in claim 1 wherein the arms and recesses are located on one side of the base.

3. A tissue expander as in claim 2 wherein the arms extend in the same direction.

4. A tissue expander as in claim 3 wherein the other side of the base is generally smoothly convex.

5. A tissue expander as in claim 1 including two like end arms located at opposite ends of the base and a central arm, the central arm being longer than the end arms.

6. A tissue expander as in claim 1 wherein the ends of the arms are smoothly rounded.

7. A tissue expander as in claim 6 wherein said port means is located in the cover.

8. A tissue expander including a base having a pair of spaced like arms, a central arm located between the like arms, and a pair of recesses each located between the central arm and one like arm, a cover overlying the base and joined to the peripheral edge of the base, and an injection port for introducing fluid into the interior of the expander.

9. A tissue expander as in claim 8 wherein the base is elongate, the arms are located on one side of the base and extend away from the base in generally the same direction.

10. A tissue expander as in claim 9 wherein the ends of the arms are smoothly rounded.

11. A tissue expander as in claim 10 wherein the cover flatly overlies the base when the expander is collapsed.

12. A tissue expander as in claim 10 wherein the central arm is longer than the like arms.

13. The method of treating male temple baldness using a soft tissue expander comprising the steps of:
    (a) forming an incision along the anterior hairline around the temple bald recesses and the forelock;
    (b) forming a pocket posteriorly of said incision beneath hair bearing scalp;
    (c) inserting a single chamber tissue expander within the pocket with concave portions of the expander surrounding the temple bald recesses;
    (d) closing the incision;
    (e) inflating the expander and expanding the overlying hair bearing scalp;
    (f) collapsing the expander, reopening the incision and removing the tissue expander from the pocket;
    (g) removing the bald scalp from the temple bald recesses;
    (h) advancing the hair bearing scalp forwardly to cover the former bald areas; and
    (i) applying the advanced hair bearing scalp to underlying tissue.

14. The method of claim 13 including the step of advancing expanded hair bearing scalp anteriorly at the forelock.

15. The method of claim 13 including the step of forming a concave hairline to either side of the forelock.

* * * * *